US00PP28281P2

(12) United States Plant Patent
Hansen

(10) Patent No.: US PP28,281 P2
(45) Date of Patent: Aug. 15, 2017

(54) ***LAGERSTROEMIA* PLANT NAMED 'CHERRY MOCHA'**

(50) Latin Name: ***Lagerstroemia* (L.) hybrid**
Varietal Denomination: Cherry Mocha

(71) Applicant: Hans A. Hansen, Zeeland, MI (US)

(72) Inventor: Hans A. Hansen, Zeeland, MI (US)

( * ) Notice: Subject to any disclaimer, the term of this patent is extended or adjusted under 35 U.S.C. 154(b) by 0 days.

(21) Appl. No.: 14/999,736

(22) Filed: Jun. 21, 2016

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Annette Para

(57) ABSTRACT

The new and distinct crape myrtle plant named *Lagerstroemia* 'Cherry Mocha' has a dense, compact, narrow, upright habit, is ground hardy to at least USDA zone 6, has glossy burgundy foliage slowly developing into deep green with burgundy tinting. The flowers are fragrant, large and cherry-red colored arising from shiny red buds.

2 Drawing Sheets

Genus and species of plant claimed: *Lagerstroemia* (L.) hybrid.

Variety denomination: 'Cherry Mocha'.

BACKGROUND OF THE INVENTION

The present invention relates to a new and distinct cultivar of *Lagerstroemia* plant, commonly known as crape myrtle, and hereinafter referred to by the cultivar name 'Cherry Mocha' or the "new plant." 'Cherry Mocha' is grown primarily as an ornamental for landscape use and for use as a potted plant and is the result of an ongoing breeding program to produce new and improved garden worthy plants for the ornamental market. The new plant was the result of open-pollinated seed collected by the inventor in fall of 2010 at a cultivated landscape in Raleigh, N.C., USA using P×WC 04-02 (not patented) as the seed or female parent. The male or pollen parent is unknown, but may have been any one of a number of hybrids or cultivars in the breeding area.

No plants of *Lagerstroemia* 'Cherry Mocha' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Lagerstroemia* 'Cherry Mocha' was initially asexually propagated by stem cuttings at a wholesale perennial nursery in Zeeland, Mich., USA in 2012. The resultant plants from successive generations have demonstrated that the new plant has remained stable and true to type in multiple generations of asexual propagation.

SUMMARY OF THE INVENTION

Plants of the new cultivar 'Cherry Mocha' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Cherry Mocha'. Among the characteristics in combination which distinguish 'Cherry Mocha' as a new and distinct cultivar, unique from all other cultivars known to the inventor are:

1. Dense, compact, upright to slightly outright growth habit;
2. Semi-glossy foliage emerges burgundy red and slowly matures to deep green with burgundy tinting;
3. Burgundy-colored stems;
4. Bright cherry-red flowers open from shiny red buds;
5. Resistance to *Cercospora* leaf spot and *Erisphe* powdery mildew;
6. Ground hardy to at least USDA hardiness zone 6.

'Cherry Mocha' is distinguished from its female parent, P×WC 04-02, with flowers that are more red and darker, burgundy-tinted foliage.

The most similar cultivars known to the inventor include: 'PIILAG-III' U.S. Plant Pat. No. 23,178, 'Trured' U.S. Plant Pat. No. 18,646 and 'Whitt VII' U.S. Plant Pat. No. 14,975. 'Cherry Mocha' is shorter and narrower than 'PITLAG-III' and has more purplish tinting in the flower. Flower color is very similar to 'Trured', but this comparison variety develops into a small tree and is much larger than the new plant. 'Whitt VII' is slightly larger in habit and has more grey in the flower color than the new plant.

BRIEF DESCRIPTION OF THE DRAWINGS

The accompanying color photographs illustrate the flower and foliage characteristics and the overall appearance of 'Cherry Mocha', showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
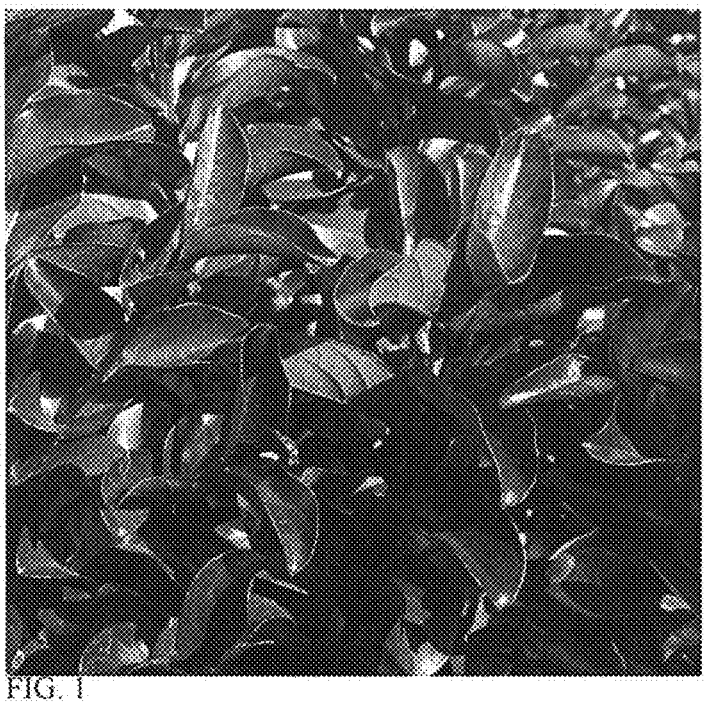
FIG. 1 shows a close-up of the young expanding foliage.
Figure 2:
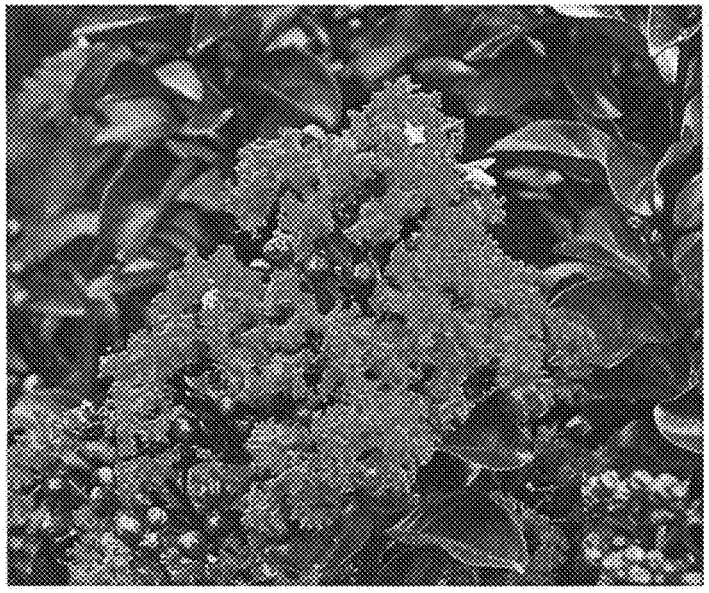
FIG. 2 shows a close-up for the flowers and buds.
Figure 3:
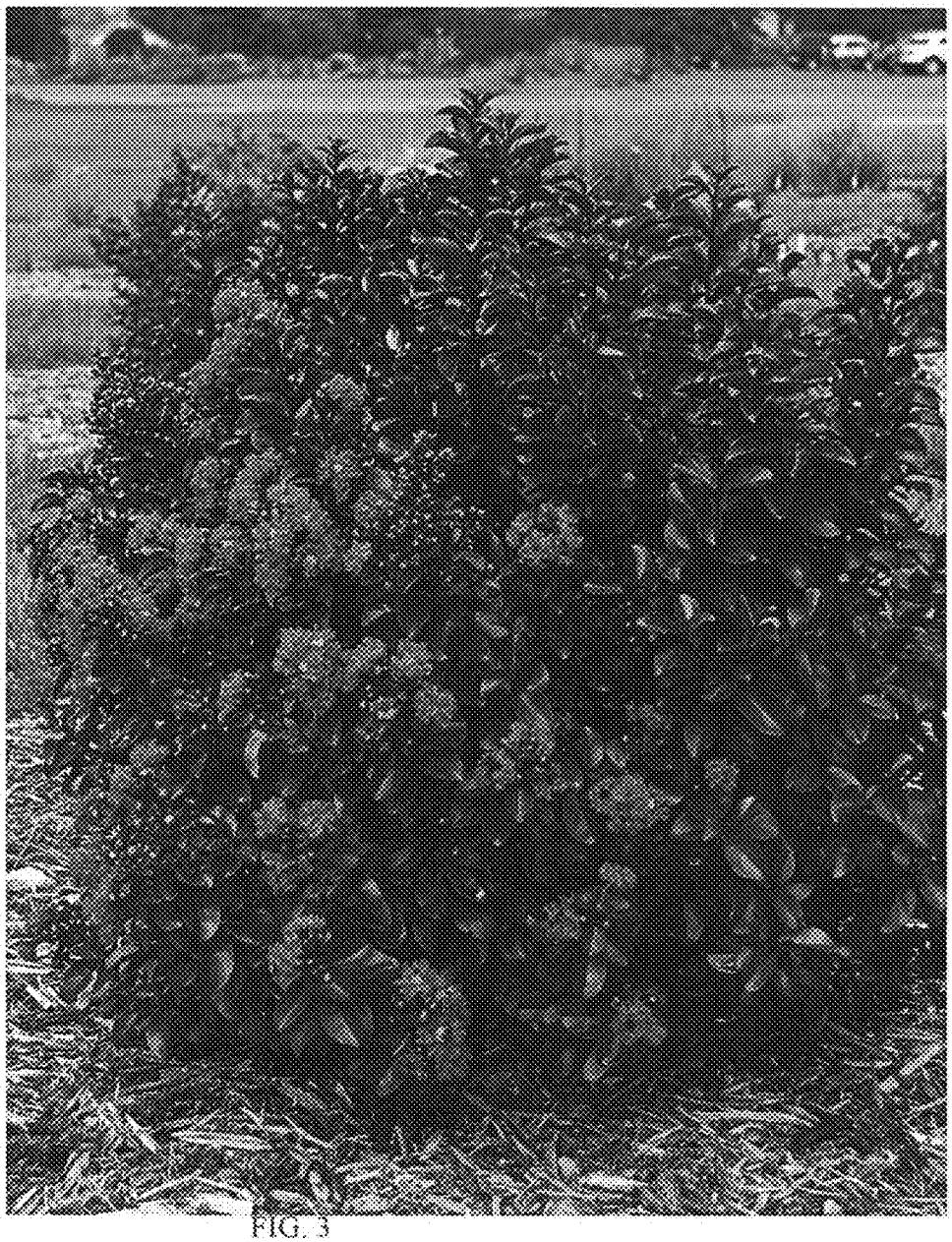
FIG. 3 illustrates a three-year-old plant in a landscape in late summer peak flowering.

The following color references are based on The 2001 edition of The Royal Horticultural Society Colour Chart except where common dictionary terms are used. The following observations and size descriptions are of approximately two-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* L.

Parentage: Female, or seed, parent P×WC 04-02; the male, or pollen parent is unknown (open-pollinated).

Propagation: Terminal softwood stem cuttings.

Time to initiate roots: About three weeks.

Growth rate: Moderate; about 10 weeks to finish and flower in a 3.7 liter container from a 65 mm liner.

Plant description: Deciduous, woody, narrow, compact flowering shrub; about six mainly upright to outward primary stems; freely branched.

Root description: Fine, numerous, fibrous, well-branched.

Plant habit: About 85 cm high from the soil level to the top of the inflorescences; about 70 cm wide with no pinching, pruning or plant growth regulators.

Stems: To about 85.0 cm long and about 12.0 mm diameter at base, terete; young stems terete and four longitudinal carinae, along line on either side of petioles.

Stem color: Woody basal 15 cm of nearest RHS 199C with exfoliating striations of nearest RHS 200C; young developing stems blend between RHS 46A and RHS 187C with intense light and nearest RHS 138B in heavily shaded regions, with carinae between RHS 187B and RHS 187C.

Node: About 20 to 25 per main stem; internode length average about 1.2 cm in young stems.

Node color: Same as surrounding stem.

Foliage description: Sub-opposite to alternate, simple, elliptical; margin ciliolate, slightly involute; acuminate apex; rounded to cuneate base; to about 5.8 cm long and about 3.4 cm wide; average about 5.4 cm long and 3.2 cm wide; adaxial and abaxial glabrous and lustrous; maintaining a burgundy color for much of the growing season.

Abaxial leaf color: Young emerging leaf nearest RHS 183A; mature leaf nearest RHS 138A with tinting of nearest RHS N186C.

Adaxial leaf color: Young emerging foliage nearest RHS 187A; mature leaf between RHS 147A and RHS 137B.

Adaxial and abaxial ciliate margin color: Nearest RHS 187B throughout season.

Veins: Pinnate, puberulent adaxial and abaxial.

Vein color: Young emerging leaf adaxial midrib and lateral veins nearest RHS 187A; young emerging leaf abaxial midrib and lateral veins between RHS 187A and RHS 187B; mature adaxial midribs and lateral veins nearest RHS 186A; mature abaxial midribs and lateral veins between RHS 187A and RHS 187B.

Petiole: Adaxial puberulent, slightly puberulent abaxial; slightly applanate adaxial; about 2.0 mm long and 2.0 mm across.

Petiole color: Young adaxial and abaxial nearest RHS 187A, mature adaxial and abaxial nearest RHS 147A blushed with nearest RHS 187B.

Inflorescence: Panicle; terminal panicles up to about 100 flowers; average about 50 flowers; up to about 16.5 cm long and about 12.0 cm across; beginning late-summer and continuing until fall, for about eight weeks.

Buds: Globose with slightly cuspidate apex and rounded base; laevigate; glabrous; about 9.0 mm tall and about 8.0 mm diameter one day prior to opening.

Bud color: Between RHS 187B and RHS 187C.

Flowers: Perfect; regular; actinomorphic; terminal panicle; individually about 2.5 cm across and about 20.0 mm tall; lasting about two days.

Flower fragrance: Sweet, light.

Peduncle: Terete with four longitudinal carinae; about 3.5 mm diameter at base, about 16.5 cm long.

Peduncle color: Blend between RHS 46A and RHS 187C.

Pedicel: Terete, about 5.0 mm long and 1.0 mm diameter.

Pedicel color: Nearest RHS N186C.

Sepals: Fused in about the basal 4.0 mm; acute apex, entire margin; glabrous and laevigate both adaxial and abaxial; about 8.0 mm long and individually about 4.0 mm long above the fusion and about 3.0 mm wide at fusion point.

Sepal color: Adaxial basal 5.0 mm between RHS 145D and RHS 142D, distal 3.0 mm nearest RHS N186B; abaxial basal 6.0 mm nearest RHS N186C, distally nearest RHS N186B.

Petals: Six; stalked; glabrous; blade ruffled or crisped; margin crisped; blade with rounded apex and cordate to sagittate base, to about 12.0 mm across and 13.0 mm long; claw base adnate to calyx, to about 6.0 mm long and 0.5 mm diameter; overall about 1.8 cm long.

Petal color: Blade adaxial and abaxial nearest RHS 60B; claw nearest RHS 60B.

Androecium:

*Stamens*.—Total about 36 to 42; typically six longer and about 30 to 36 shorter.

*Filaments*.—Longer stamens to about 15.0 mm long and about 0.5 mm diameter, curled about 180 degrees in distal 5.0 mm; shorter filaments curled about 360 degrees in the distal 5.0 mm, about 9.0 mm long and less than 0.3 mm diameter; color of longer filaments between RHS 60B and RHS 53B.

*Anthers*.—Oblong; more developed on longer stamens to about 1.2 mm long and 1.0 mm across, on shorter stamens about 1.0 mm long and about 0.7 mm across; color nearest RHS 17B.

*Pollen*.—Abundant on longer stamens; color nearest RHS 10C.

Gynoecium: One.

*Style*.—Terete; glabrous; about 19.0 mm long and 1.0 mm diameter; color nearest RHS 53B in the middle portion, distally nearest RHS 53A and base nearest RHS 53B.

*Stigma*.—Globose; about 1.1 mm diameter; color nearest RHS 187A.

*Ovary*.—Superior; globose; about 2.0 mm tall and 2.0 mm diameter; color nearest RHS 150D.

Fruit: Globose; six-valved dehiscent capsule; about 7.0 mm wide and 7.0 mm tall; apex rostrate; base rounded.

Fruit color: Between RHS 200B and RHS 200A.

Seed: Lunate; about 5.0 mm long and 2.0 mm across at widest point.

Seed color: Between RHS 165B and RHS 165C.

Disease resistance: *Lagerstroemia* 'Cherry Mocha' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

I claim:

1. A new and distinct cultivar of crape myrtle plant named *Lagerstroemia* 'Cherry Mocha' essentially as herein illustrated and described.

* * * * *